United States Patent
Prasad et al.

(10) Patent No.: US 12,076,143 B2
(45) Date of Patent: Sep. 3, 2024

(54) WEARABLE BIOSENSORS WITH ROOM TEMPERATURE IONIC LIQUID BUFFER

(71) Applicants: EnLiSense LLC, Allen, TX (US); Board of Regents, The University of Texas System, Austin, TX (US)

(72) Inventors: Shalini Prasad, Allen, TX (US); Sriram Muthukumar, Allen, TX (US)

(73) Assignees: EnLiSense, LLC, Allen, TX (US); Board of Regents, The University of Texas System, Austin, TX (US)

( * ) Notice: Subject to any disclaimer, the term of this patent is extended or adjusted under 35 U.S.C. 154(b) by 939 days.

(21) Appl. No.: 16/124,164

(22) Filed: Sep. 6, 2018

(65) Prior Publication Data

US 2019/0069818 A1    Mar. 7, 2019

Related U.S. Application Data

(60) Provisional application No. 62/554,841, filed on Sep. 6, 2017, provisional application No. 62/554,956, filed on Sep. 6, 2017.

(51) Int. Cl.
*A61B 5/1477* (2006.01)
*A61B 5/145* (2006.01)
*A61B 5/00* (2006.01)

(52) U.S. Cl.
CPC ........ *A61B 5/1477* (2013.01); *A61B 5/14517* (2013.01); *A61B 5/0002* (2013.01); *A61B 5/6833* (2013.01)

(58) Field of Classification Search
CPC .......................... A61B 5/14517; A61B 5/1477
See application file for complete search history.

(56) References Cited

U.S. PATENT DOCUMENTS

| | | | | |
|---|---|---|---|---|
| 2009/0293590 A1* | 12/2009 | Zeng | .................. | G01N 27/4162 73/24.06 |
| 2010/0044224 A1* | 2/2010 | Kataky | ............ | G01N 33/48707 204/403.13 |
| 2015/0014164 A1* | 1/2015 | Lee | ...................... | G01N 27/302 204/412 |
| 2016/0166186 A1* | 6/2016 | Ferguson | ........... | A61B 5/14546 600/352 |

OTHER PUBLICATIONS

Wang et al. Zinc oxide nanocomb biosensor for glucose detection, Appl. Phys. Lett. 88, 233106 (2006) (Year: 2006).*

(Continued)

*Primary Examiner* — Tse W Chen
*Assistant Examiner* — Michael A Catina
(74) *Attorney, Agent, or Firm* — Aambell PC

(57) ABSTRACT

A biosensor device includes a porous substrate, where the substrate comprises semiconductor elements functionalized to conjugate with a particular analyte, the semiconductor elements are embedded within at least a portion of the substrate, and the substrate is to absorb fluid capable of carrying the particular analyte. The device further includes two or more electrodes attached to the substrate to correspond to the portion of the substrate, where the portion of the substrate further comprises Room-Temperature Ionic Liquid (RTIL).

19 Claims, 12 Drawing Sheets

(56) References Cited

OTHER PUBLICATIONS

Munje, R.D., Muthukumar, S., Jagannath, B. et al. A new paradigm in sweat based wearable diagnostics biosensors using Room Temperature Ionic Liquids (RTILs). Sci Rep, Jul. 1950 (2017) (Year: 2017).*

Pauliukaite, R., Doherty, A., Murnaghan, K. and Brett, C. . (2008), Application of Some Room Temperature Ionic Liquids in the Development of Biosensors at Carbon Film Electrodes. Electroanalysis, 20: 485-490. (Year: 2008).*

* cited by examiner

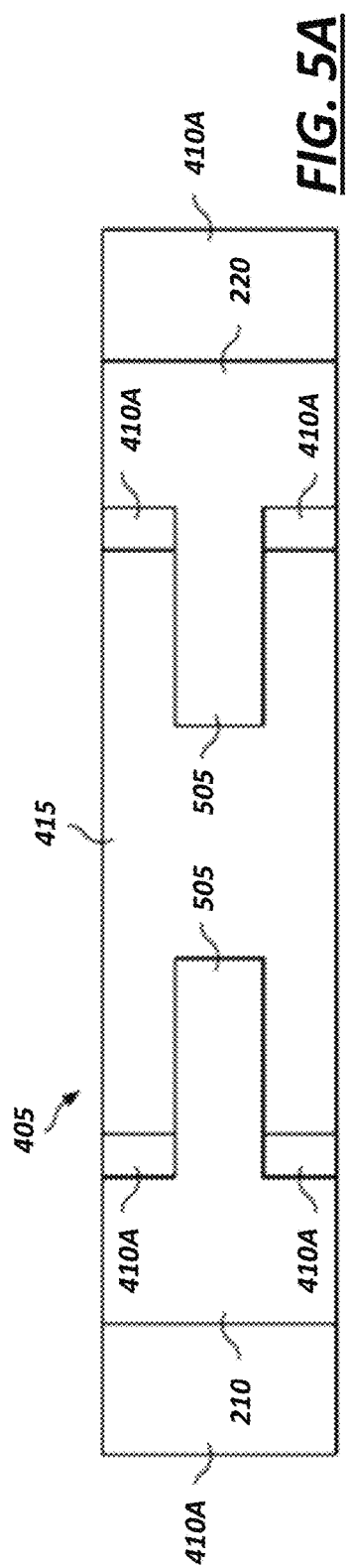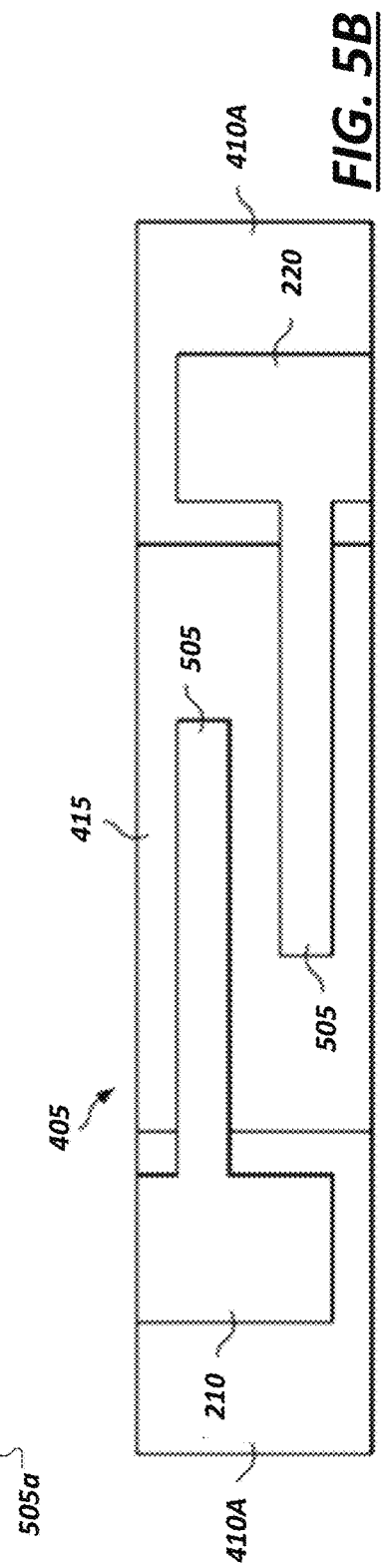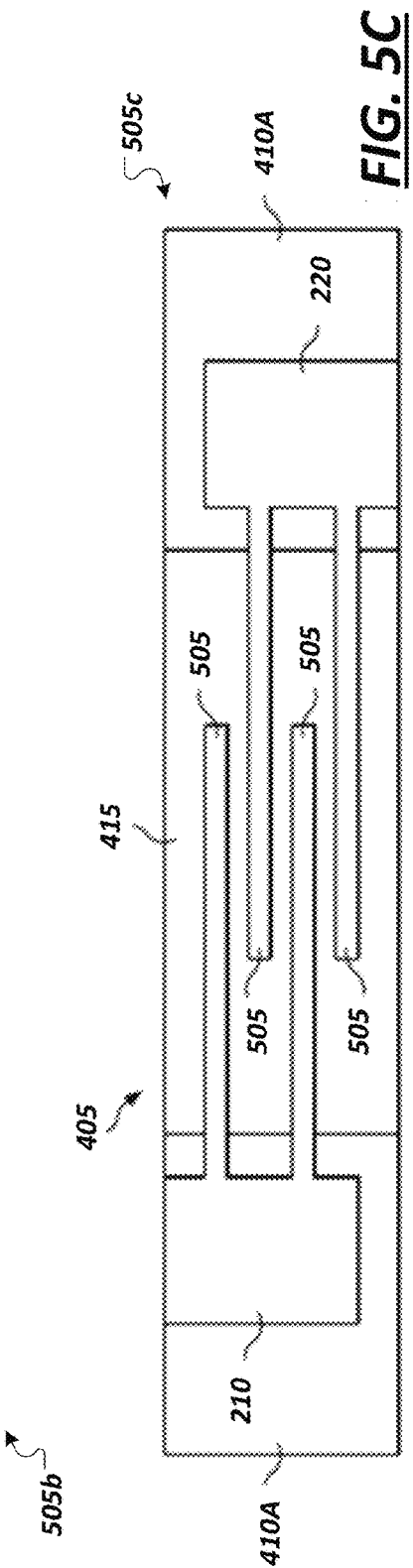

| Parameter | Value |
|---|---|
| Polymer pore diameter | ~ 200 nm |
| Polymer pore density | 41 % |
| Polymer thickness | 110 μm |
| ZnO thin film thickness | ~ 100 nm |
| ZnO grain diameter | 20 nm |
| ZnO surface roughness | 16.9 nm |

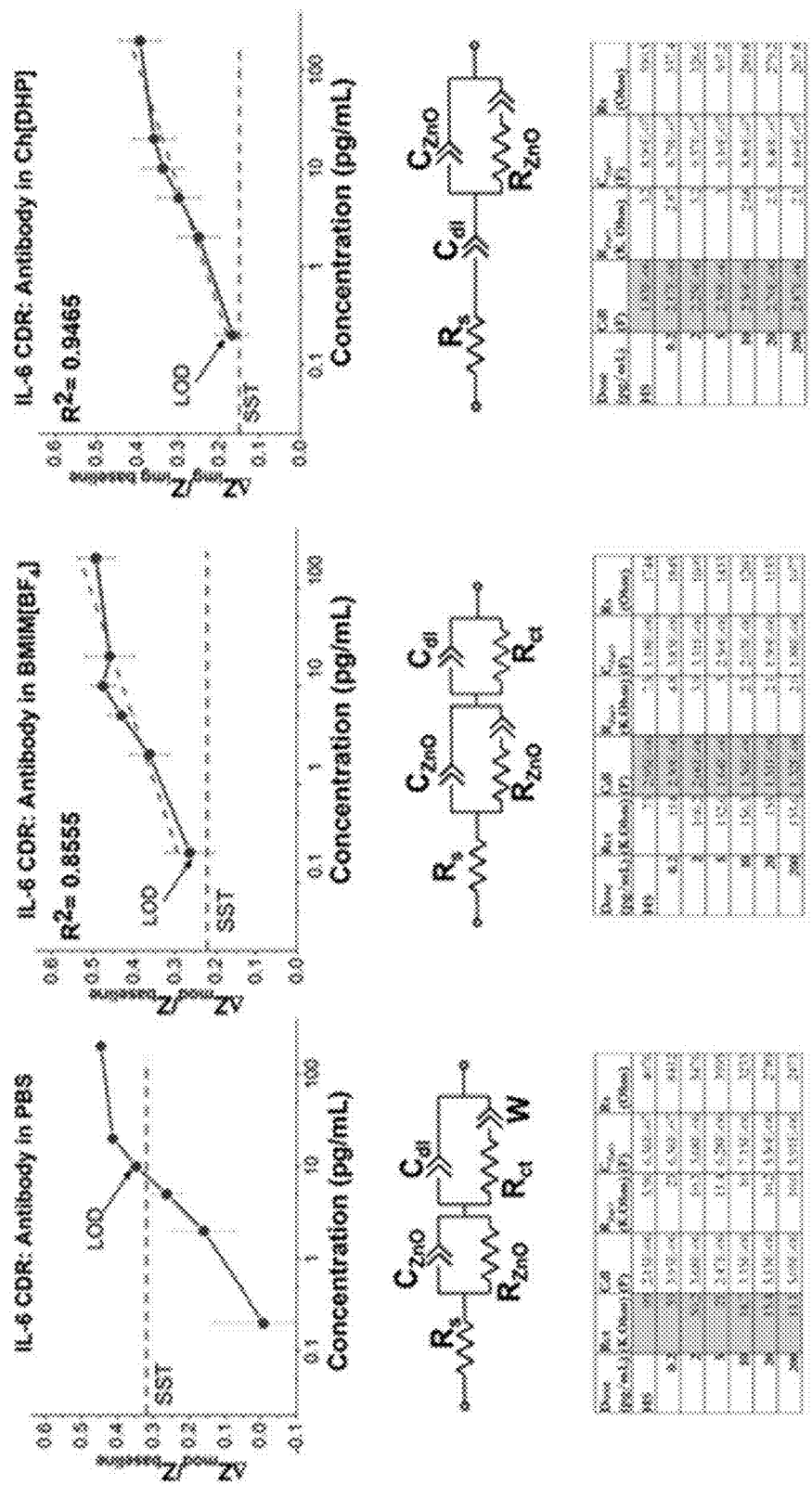
*FIG. 8A*  *FIG. 8B*  *FIG. 8C*

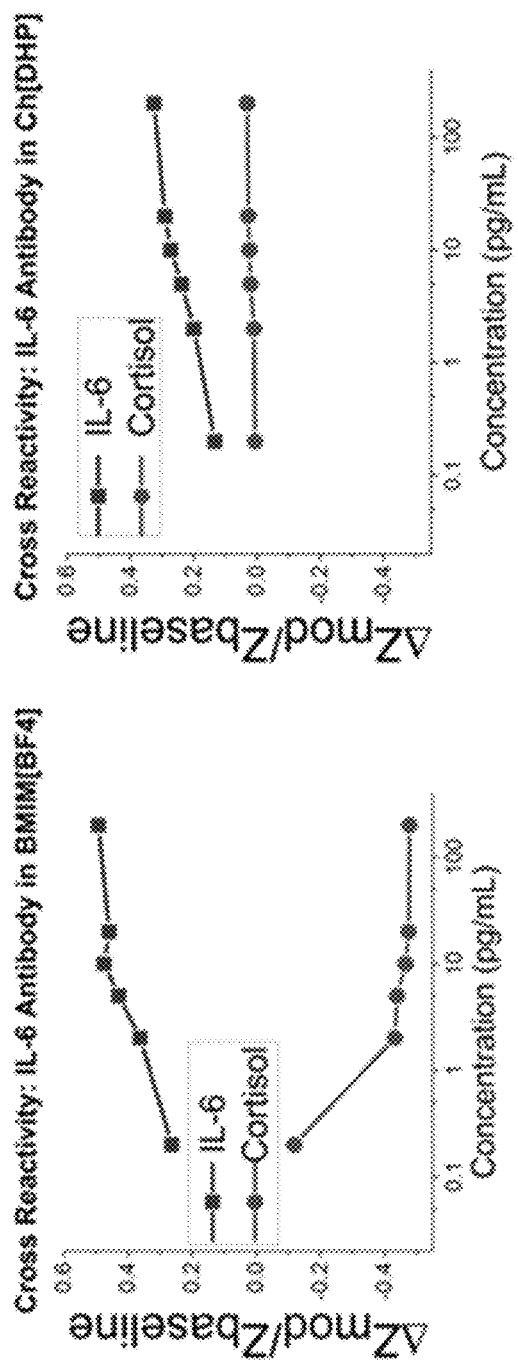
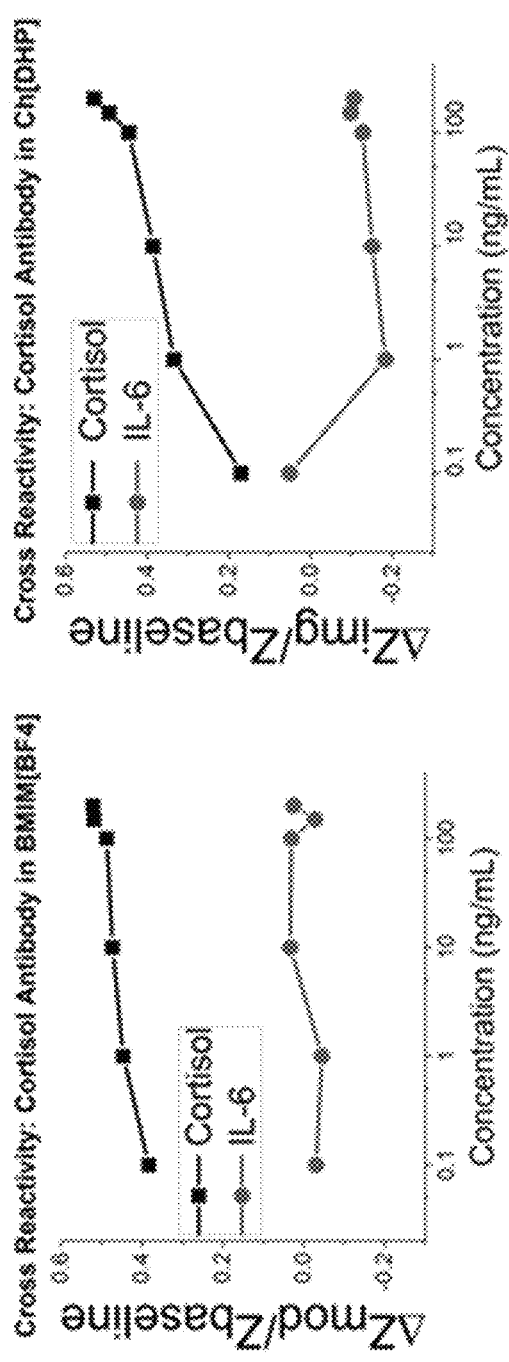
FIG. 9A
FIG. 9B

WEARABLE BIOSENSORS WITH ROOM TEMPERATURE IONIC LIQUID BUFFER

This application claims benefit to U.S. Provisional Patent Application Ser. No. 62/554,841, filed Sep. 6, 2017 and U.S. Provisional Patent Application Ser. No. 62/554,956, filed Sep. 6, 2017, which are incorporated by reference herein in its entirety.

BACKGROUND

The present disclosure relates in general to the field of sensor devices, and more specifically, to wearable biosensors.

Biosensor systems include analytic devices that are capable of detecting and, in many cases, estimating the relative concentration of specific substances, commonly called analytes, and other parameters of biological interest. The analytes detected can be both inorganic or organic in nature. Biosensor systems provide a response that is modulated by the presence of one or more specific analytes in order to provide information to a user that an analyte is present in the system and possibly an estimate of the concentration of the analyte.

BRIEF DESCRIPTION OF THE DRAWINGS

FIGS. 5A-5C are diagrams illustrating example electrode configurations of a biosensor device in accordance with at least some embodiments.

FIGS. 8A-8C are graphs illustrating performance of an example RTIL-infused biosensor.

FIGS. 9A-9B are graphs illustrating performance of an example RTIL-infused biosensor.

Like reference numbers and designations in the various drawings indicate like elements.

DETAILED DESCRIPTION

Biosensors for consumer wearable devices is an emerging field with the promise of facilitating multiplexed physiological monitoring for quantitative assessment of body functions. Highly functional wearable biosensors that can also provide meaningful diagnostics to guide therapeutics would be extremely valuable to end-user consumers or health-professionals. In order to make wearable biosensors as successful consumer products it is important to demonstrate enhanced multiplexed functionality, reliability, and ease-of-use through non-invasive monitoring of body fluids. In some implementations, physiological monitoring may benefit from monitoring and sensing various non-invasive body fluids, which may be actively and/or passively expressed, such as sweat, saliva, tears, gingival crevicular fluid (GCF), and urine, among other examples. These body fluids contain a plethora of medical information and are capable of stimulation, collection, and being analyzed. Sensors capable of simultaneously detecting of multiple different electrolytic ions such as Na, K, Cl, and Ca in addition to metabolites, proteins and other biomolecules may have particular utility. However, traditional wearable, non-invasive biosensors, both in the commercial and research domain, primarily detect only an electrolyte, a single protein, an enzyme or metabolite biomolecule at a time. Serial or Simultaneous detection of multiple analytes on a single platform as described in this disclosure does not exist.

Figure 1:
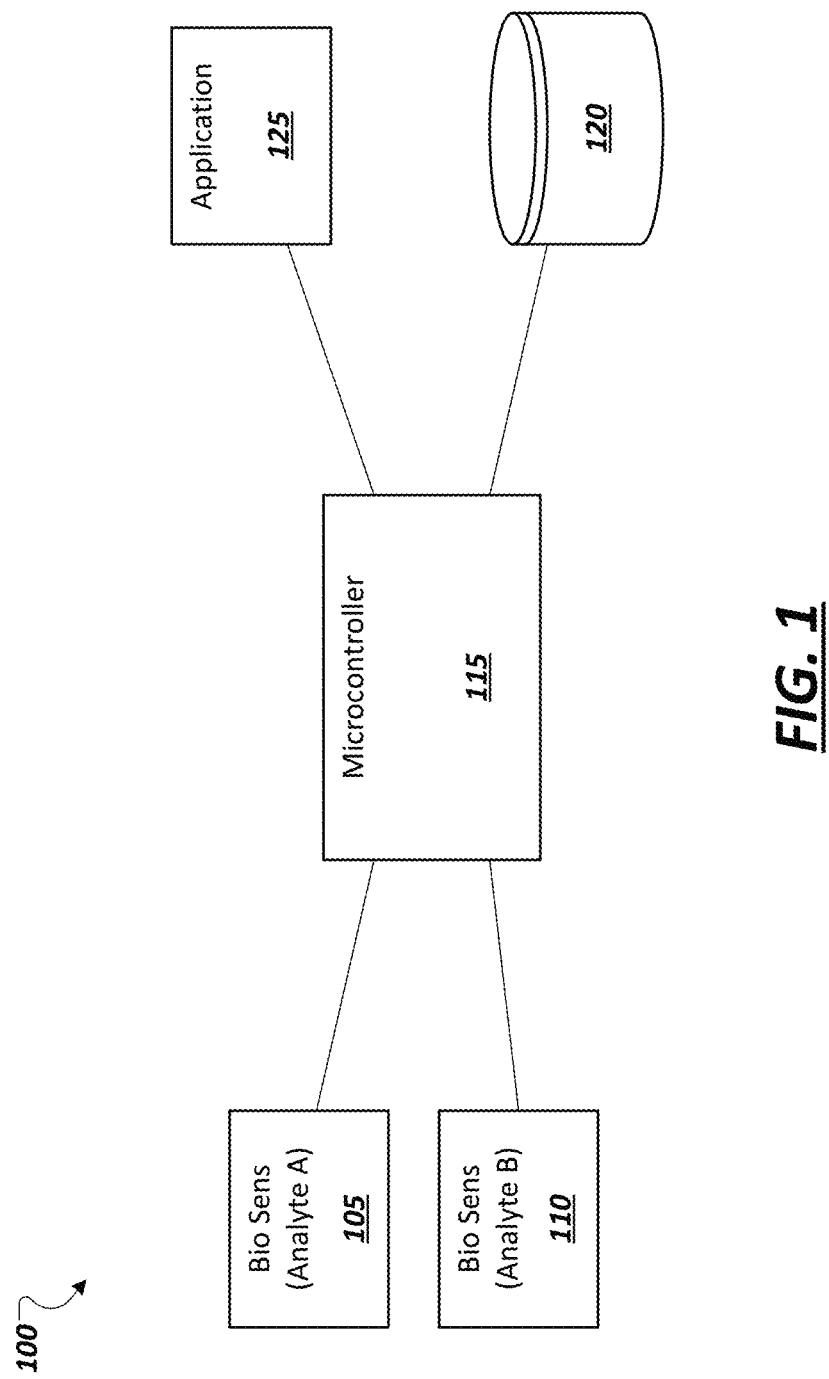
FIG. 1 illustrates a simplified schematic diagram of an example computing system including one or more biosensors.

Noninvasive body fluid based wearables and sensing devices may be provided, which may be attached to the body of a human or animal for biomarker monitoring with multiple measurements (e.g., over a 24 hour or other period). A biosensor device may further include the ability to process data and wirelessly (or through wires) communicate to other devices and/or to a cloud server enabling data storage and consumption of the information obtained from the biosensor (e.g., using one or more applications and services). For instance, such a system, such as illustrated in FIG. 1, may be used to implement anytime-anywhere medical diagnostic devices. For instance, as shown in the simplified block diagram 100 of FIG. 1, one or more such sensors 105, 110 may be provided, such as features implemented in accordance with the discussion herein. The sensors may connect to one or more microcontroller data processors 115 via a direct wireline connection or via a wired or wireless data network. The biosensors may provide information, which may be processed by the microcontroller. The microcontroller may provide sensor data for storage in one or more data storage elements (e.g., 120) and for consumption by various local and/or remote software applications and services (e.g., 125), among other example features and systems.

In some implementations, advancing wearable biosensors as reliable diagnostics devices may involve improving upon the stability and reliability of the materials constituting the sensor, such as during prolonged and continuous exposure to body fluids. For instance, enhancing the stability of affinity-based capture probes may enable the prolonged functionality and performance of wearable diagnostic biosensors. As an example, the biochemical integrity of these capture probes may be maintained during the continuous and prolonged exposure to sweat in order to report multiple measurements in a 24 hour or longer period. Several strategies involving surface modification of the sensor and/or the capture probes adopted to retain the chemical integrity of the capture probes have been unsuccessful in traditional applications. For instance, prior solutions have struggled with the retention of the chemical structure of the capture probes which may be essential for achieving stable and repeatable sensing of the target biomarker. Hence, the development of wearable non-invasive diagnostics tools, which are capable of quantifying more than one molecule with high precision in a multiplexed manner and with long term stability to support continuous/dynamic monitoring may be extremely beneficial for managing diseases, provide customized therapies, and reduce the total cost burden on the consumer, among other example benefits.

Biosensors may be provided to detect the presence of various analytes in various bodily fluids. For instance, sweat may be collected and assessed using an example sensor. Sweat, as a test fluid, can contain 99% water, with typical solutes including Na+, Cl', K+, NH4+, alcohols, lactates, peptides, and proteins, among other examples. The typical pH range for a normal healthy person may be 4.5 to 7.0. However, different regions of the body may have different sweat gland density ranging from 21-540 glands per $cm^2$. A typical sweat rate range for a normal adult of ~1-20 nL/min/gland. A biosensor may be provided, for instance, to perform real-time monitoring and should be stable for a period of up to 12 to 24 hours. This stability should be maintained, in some examples, for the range of temperatures expected on a human body. For instance, although core body temperature is typically at 37 deg C., different regions of the body can exhibit different temperatures lower than the core body temperature. As sweat may include multiple different analytes, real-time and continuous monitoring of multiple analytes in sweat may be provided in an example system to provide non-invasive point-of-care diagnostic devices. Such devices may be also provided and utilized to detect various biomarkers associated with disease and health conditions in other fluids, such as tears, saliva, urine, GCF, etc. Additionally, the sensor may be configured to capture and detect miniscule amounts (e.g., at the nL level) of fluid to enable passive monitoring, as well as capture and detect larger amounts of fluid to enable active monitoring using the improved biosensor device.

In some implementations, Room Temperature Ionic Liquids (or "RTILs") may be utilized to enhance example biosensors, such as described herein. RTILs have the ability to enhance the stability of biomolecules such as proteins and enzymes. RTILs may be utilized, for instance, in protein extraction, purification, stability, and many other applications related to enzymes, amino acids, and peptides. RTILs possess low volatility, wide electrochemical window, and high thermal and chemical stability over conventional solvents. These properties of RTILs can be modulated by the optimal choice of cationic and anionic moiety towards enhancing protein conformational stability. In some implementations, RTILs containing caotropic (e.g., large-sized and low-charged, weakly hydrated ions that decrease the structure of water) cations and kosmotropic (e.g., small-sized and high-charged, strongly hydrated ions that increase the structure of water) anions may optimally stabilize the biological macromolecules. Since the net charge of proteins depends on parameters such as the pH of the solution, both RTIL cations and anions may be considered in discussing ion-protein interactions. The disruptions to charge and hydrogen bonding networks within RTIL formulations can manifest antimicrobial and antifungal properties, non-toxicity to cells, and for transdermal drug delivery and pathogen neutralization, among other example features and advantages.

RTILs, as a class of compounds, possess a unique combination of properties (high charge density, electrochemical stability, low/negligible volatility, tunable polarity, etc.). There is no solvent in a neat RTIL electrolyte, unless it is deliberately added or they absorb water from the environment, the molecular RTILs ions are neither small (on an atomistic scale) nor roundish, and their molecular charge density is highly nonuniform. This means that the effects of short-range ion-to-ion interactions, molecular shape of ions, and ion molecular charge distribution are very important for their properties both in the bulk and at interfaces. Although these RTILs are molten salts at room temperature consisting of poorly coordinated ions, each RTIL is an overall neutral assembly of charged particles. As the majority of their applications deal with their behavior near interfaces and, particularly as in this proposal, near electrified interfaces, understanding the charge and electric potential distribution in RTILs at charged semiconducting oxide interfaces is crucial for understanding their performance as electrolytes for electrochemical sensing applications.

Most biomolecules have a well-defined electrostatic signature, and their interaction with electrolytes is predominantly with one of the two ions. For instance, lipids absorb cations; proteins and peptides select their partner according to a charge that depends on chemical parameters such as pH of the physiological solution; nucleic acids are negatively charged and therefore attract cations; sugars have a clear tendency to donate hydrogen bonds and preferentially bind anions, among other examples. The size and complexity of the RTIL ions, however, imply that dispersion and steric, but also electrostatic polarization interactions, play a role that, although second to bare Coulomb, is by no means negligible. Particularly in the case of protein biomolecules, these effects decide the caotropic or kosmotropic effect of RTIL ions. RTILs containing caotropic (large-sized and low charged, weakly hydrated ions that decrease the structure of water) cations and kosmotropic (small-sized and high charged, strongly hydrated ions that increase the structure of water) anions are found to optimally stabilize the biological macromolecules. Since the net charge of proteins may depend on parameters such as the pH of the solution, both RTIL cations and anions may be considered in discussing ion-protein interactions. Salting-out power implies the tendency of proteins to correct folding and relative ordering, while enhanced solubilization (salting-in) might be the first step toward unfolding and eventual aggregation into amyloids. In many cases, the cation destabilizes the structure, and stabilization can only come from an overcompensation by the anion. Neutral moieties in the cation, such as the hydrocarbon tails of [Cnmim]+, may be particularly damaging on the stability and correct folding of proteins, as shown by the increased denaturation effect of [Cnmim]+ RTILs with increasing n on the structure of bovine serum albumin, adenosine deaminase, and two different α-amylases.

In some implementations, a biosensor device may be built from a conductor/semiconductor stack. In some cases, the biosensor device may include or build upon features and functionality described in U.S. patent application Ser. No. 14/946,899, filed Nov. 20, 2015 or PCT Patent Application PCT/US17/57478, filed Oct. 19, 2017, which disclosures are each incorporated by reference herein in their entirety. In some instances, the conductor/semiconductor stack may include gold, platinum, molybdenum, and/or silver as either a single layer or a combination of layers as conducting electrode materials and further include zinc oxide (ZnO), tin oxide (SnO2), titanium oxide (TiO2), graphene oxide (GO), Molybdenum disulfide (MoS2), vanadium oxide (VO2), vanadium pentoxide (V2O3) or another semiconducting material. These conductor/semiconductor stacks may be fabricated on nanoporous structured textile, polymer surfaces, or other surfaces such as discussed herein.

In some implementations, biosensing may be achieved through detection of trace species of target analytes in body fluids adsorbed onto RTIL-wicked nanoporous membranes, with RTILs functioning as the electrolyte forming an electrical double layer (EDL) at the functionalized sensor electrode/RTIL electrolyte interface. The transport and mobility of the target analytes in the adsorbed sweat within the RTIL may be modulated using electrophoretic mechanisms to screen out non-specific species from reaching the functionalized sensor surface. The sensor surface is functionalized with the target specific protein biomolecule capture probes that may be electrically characterized to detect only for the target analytes in adsorbed sweat (or other target fluid) presented at the interface, further enhancing the specificity in detection. The proposed biosensor device may be implemented as a multiplexed array of such sensors, each independently functionalized for specific detection of a respective target analyte(s), with each sensor output/results independently measured and transduced to provide a combinatorial outcome relating to the end state being predicted. In this manner, multiple different analytes may be monitored and detected using a single sensor device including such an array of biosensors, among other example implementations.

Figures 2A, 2B:
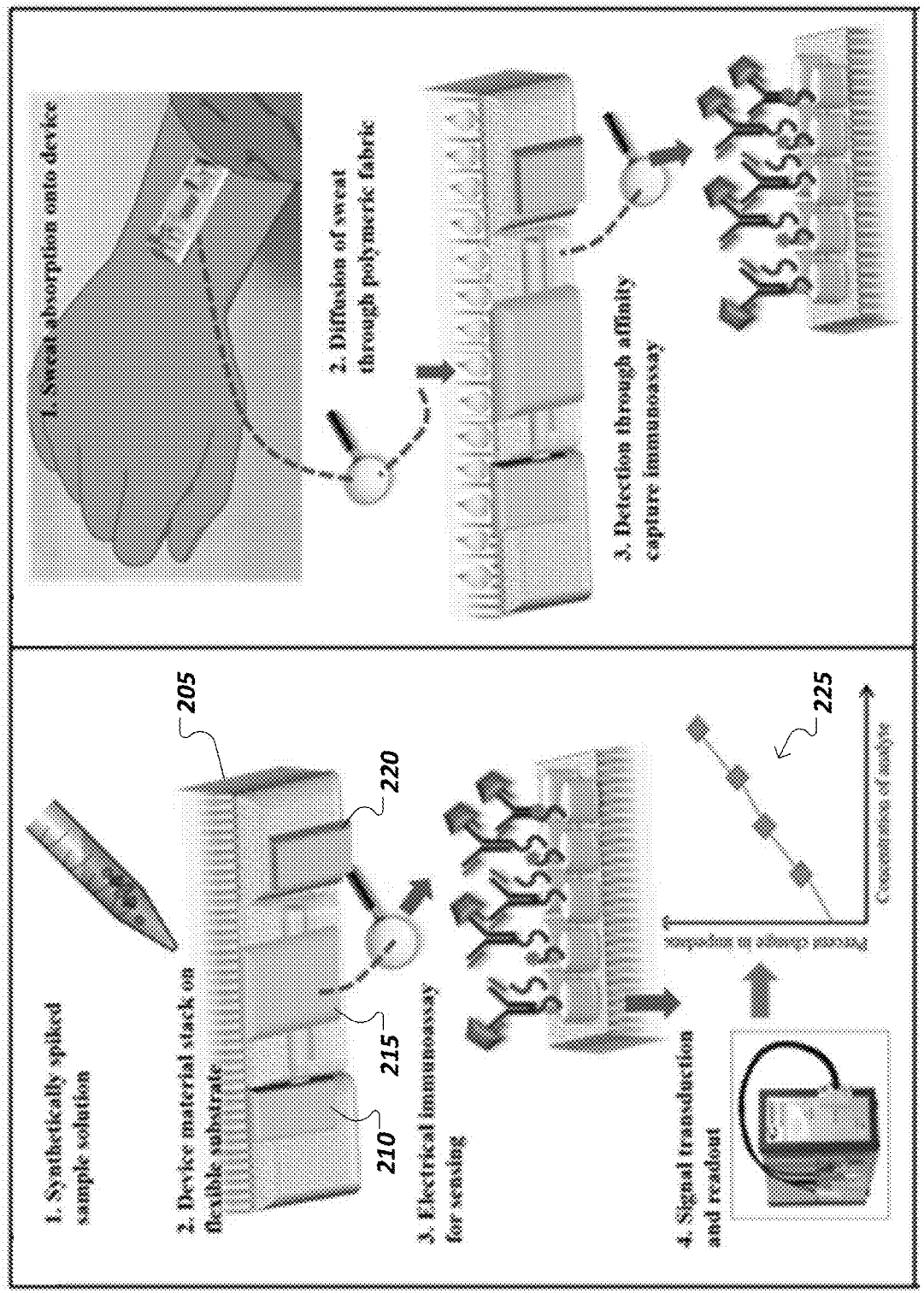
FIGS. 2A-2B illustrate simplified diagrams showing example uses of biosensor devices.

As shown in the example FIG. 2A, a simplified diagram 200a is shown illustrating example operations according to an embodiment of an example biosensing system based on principles introduced above. During operation, fluid may be brought into contact with the biosensor 205 and a voltage may be applied across two or more electrodes (e.g., 210, 215, 220) provided on the sensor. In one example, transverse electrodes may be provided, on which a transverse voltage may be applied, and orthogonal electrodes may also be provided (for a total of three electrodes) and an orthogonal voltage may be applied across the orthogonal electrodes. In such an example, the transverse voltage and orthogonal voltage may generate electric fields in mutually perpendicular directions. Upon application of an electric field between the two or more electrodes, dielectrophoresis (DEP) may be enabled, in which analyte is attracted to or repelled from a region of high electric field intensity in a direction perpendicular to the plane of transverse electrodes, thereby focusing analyte at fluid-sensor interface. In some embodiments, an AC voltage may be initially applied across transverse electrodes, enabling DEP and focusing analyte to fluid-sensor interface at sensing element; subsequent switching of the voltage across transverse electrodes from AC to DC, with the AC voltage across orthogonal electrodes facilitates formation of the EDL in fluid and modulation of current across transverse electrodes. Note that in some embodiments, the orthogonal voltage may also comprise DC voltage; in such embodiments, the modulation of the current between transverse electrodes may not be as large as with AC voltage; nevertheless, such modulation may be sufficient to enable detection of at least a single target species of analyte.

Binding of analyte to the fluid-sensor interface may be sensed (e.g., measured) through a change in impedance, capacitance, current, or voltage across sensing element based on electron-ion interactions at fluid-sensor interface. In various embodiments, output (e.g., change in impedance, current, voltage, etc.) from biosensor may vary with presence, concentration and/or other characteristic of analyte. Output may be measured using any known technique, such as potentiostat, amperometer, etc. depending on a type of output (e.g., whether change in impendence, or current, etc.).

In various embodiments, a biosensor may be initially calibrated for a specific analyte through suitable calibration steps (e.g., fluid calibration and electronic calibration). For example, fluid may comprise a liquid containing analyte in a known concentration, say $C_1$. One or more voltages may be applied across the two or more electrodes and output measured to be, say $O_1$. Output may comprise impedance in some embodiments, as illustrated in FIG. 2A. Output may also comprise any other suitable measurement, including capacitance, current, etc. In some embodiments, $O_1$ may comprise response. In other embodiments, $O_1$ may comprise a suitable combination of baseline and response. Next, concentration of analyte may be changed in fluid to another known concentration, say $C_2$. The transverse and orthogonal voltages may be applied across electrodes and output measured to be, say $O_2$. The process may be continued until a range of concentrations has been measured, from $C_1$ to $C_N$. A calibration chart (e.g., 225) may be generated with analyte concentrations $C_1, C_2, \ldots C_N$ charted against corresponding outputs $O_1, O_2, \ldots O_N$. Calibration chart may provide an expected analyte concentration (within range $C_1$-$C_N$), for a known output (within range $O_1$-$O_N$), and vice versa. After testing with an unknown analyte concentration to obtain corresponding output, say O, the calibration chart may be used to obtain the corresponding analyte concentration, C, therefrom. Although one particular calibration technique has been described herein, any suitable calibration technique may be used within the broad scope of the embodiments.

FIG. 2B is a simplified diagram 200b illustrating example operations that may be associated with an embodiment of a biosensing system. An example biosensor, such as described herein, may be attached (e.g., removably, for example, using an appropriate adhesive) to skin of a user. Actively or passively expressed sweat or other bodily fluids may diffuse through the porous membrane portion of substrate to be monitored and one or more voltages may be applied to the electrodes, resulting in electron-ion interaction between analyte (e.g., salt) in the fluid and sensing element at fluid-sensor interface. The interaction may be sensed through a change in output, which may indicate an amount of analyte in the sweat. Similar procedures may be carried other to measure any suitable secretion, including tears. In a general sense, sweat may be noisier than tears. Similar procedures may be followed for blood testing using a finger prick, similar to a glucose sensor; urine testing using a test strip comprising biosensor, similar to a typical pregnancy tester; and saliva testing with biosensor inserted into a mouth guard or similar device, among other examples.

Figure 3:
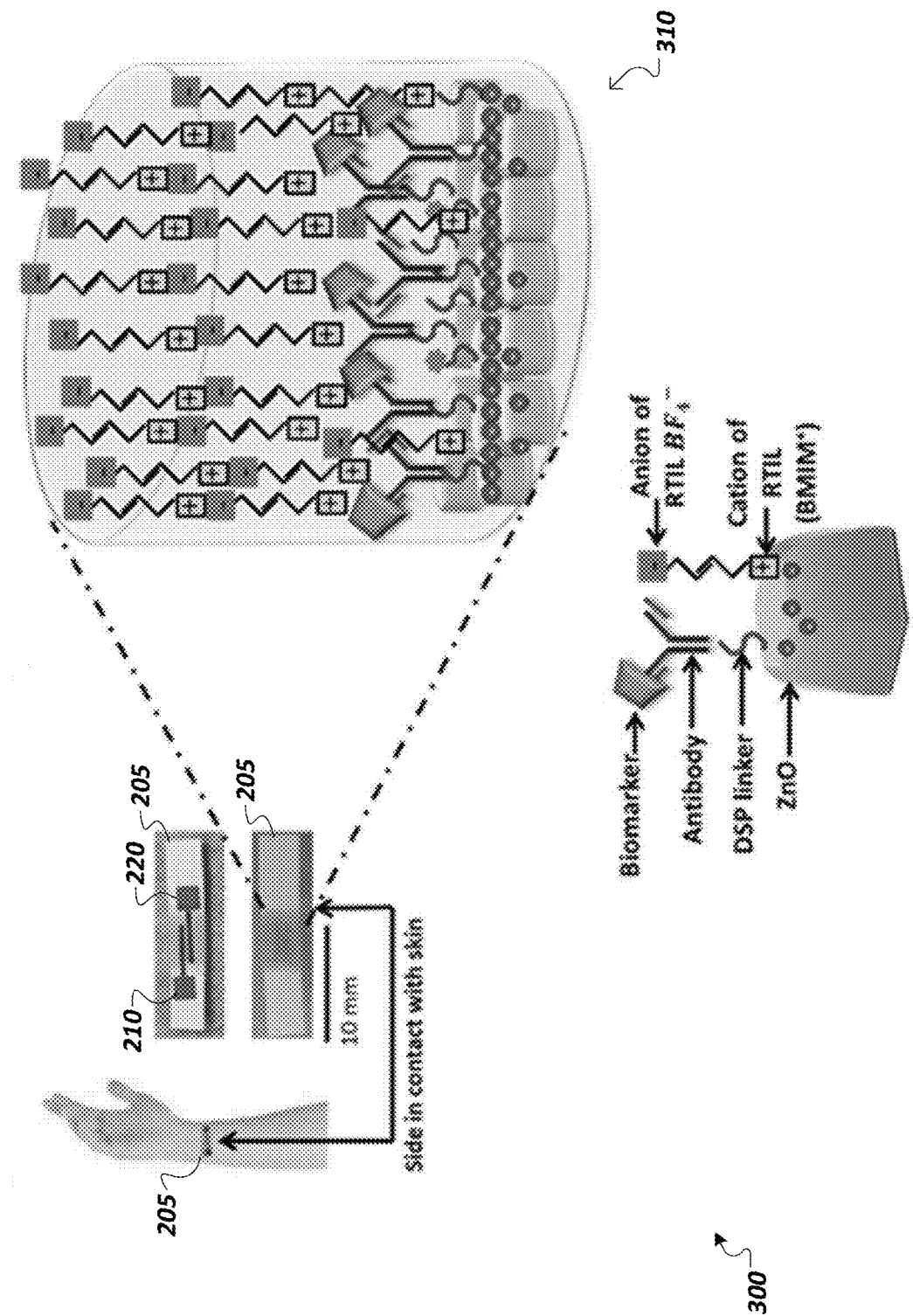
FIG. 3 illustrates a simplified schematic diagram of an example biosensor with a substrate that includes Room-Temperature Ionic Liquid (RTIL).

FIG. 3 is a simplified diagram 300 illustrating an improved sensor device 205 that is enhanced by providing RTIL on the substrate of an example biosensor device. The deposited RTIL may be absorbed into the substrate such that the two or more electrodes (e.g., 210, 220) are positioned to correspond with the deposited RTIL (e.g., 305) (as well as the antibodies provided on semiconducting particles (e.g., zinc oxide ZnO) functionalized to bind to a particular analyte).

In some implementations, providing a biosensor with RTIL, such as that discussed in connection with the examples herein, can enhance the functionality of the sensor. For instance, the sensor can be implemented as a three-electrode stack or a two-electrode stack. In the two-electrode configuration, the device may function as an impedance-based sensor where a DC or AC field is applied to measure the changes in impedance due to the interaction of the target analyte(s) in adsorbed sweat within the RTIL wicked nanoporous substrate towards the functionalized sensing surface, thus electrically screening out/in of non-specific versus specific charged species. Detection and quantification may be achieved through measuring the modulation in double layer capacitance (Cdl) and/or charge-transfer resistance (Rct) due to the affinity binding of target analyte(s) onto the sensing electrode surface (e.g., as represented at 310).

Figure 4A:
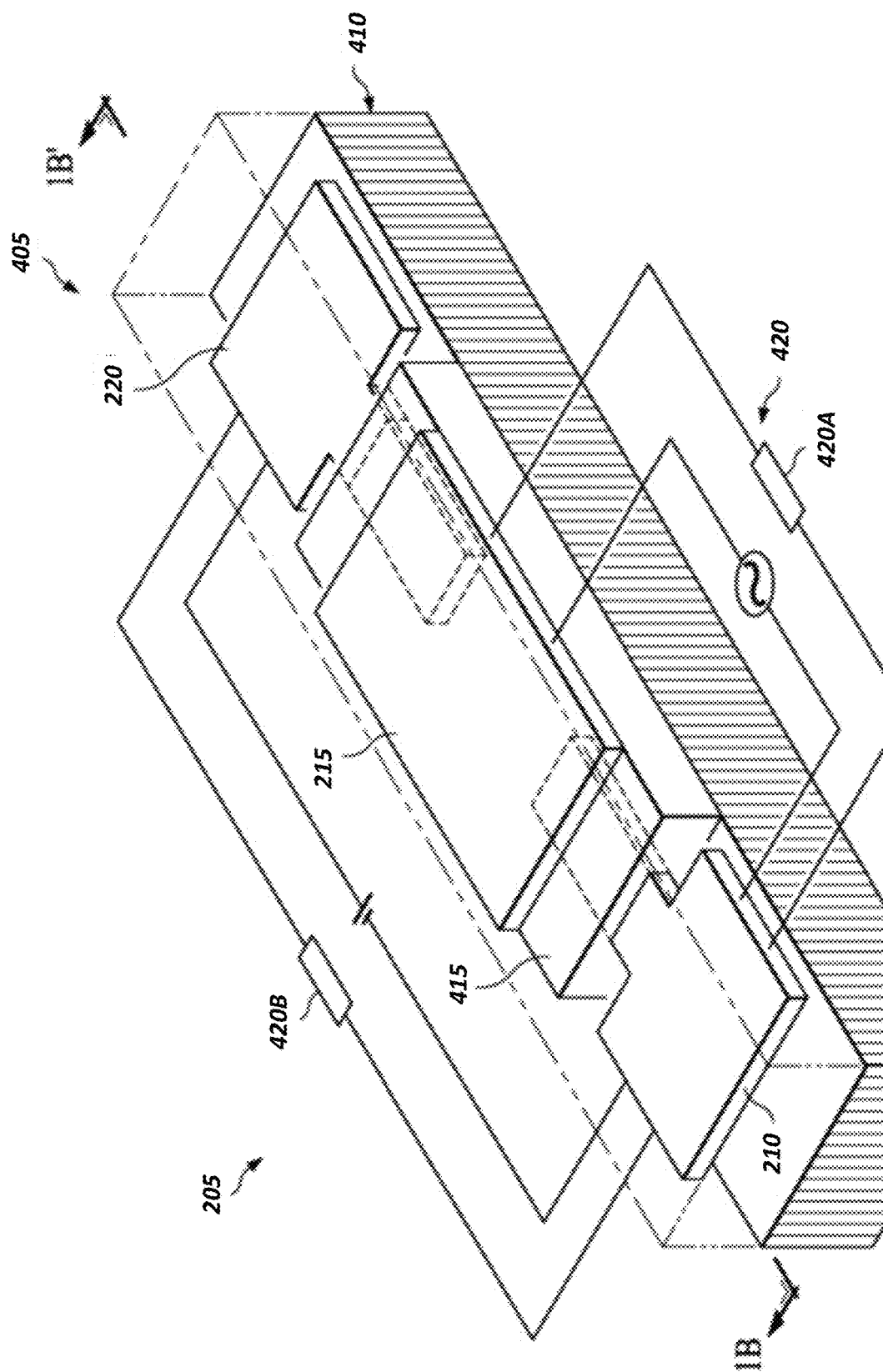
FIGS. 4A-4C are diagrams illustrating views of an example biosensor.
Figure 4B:
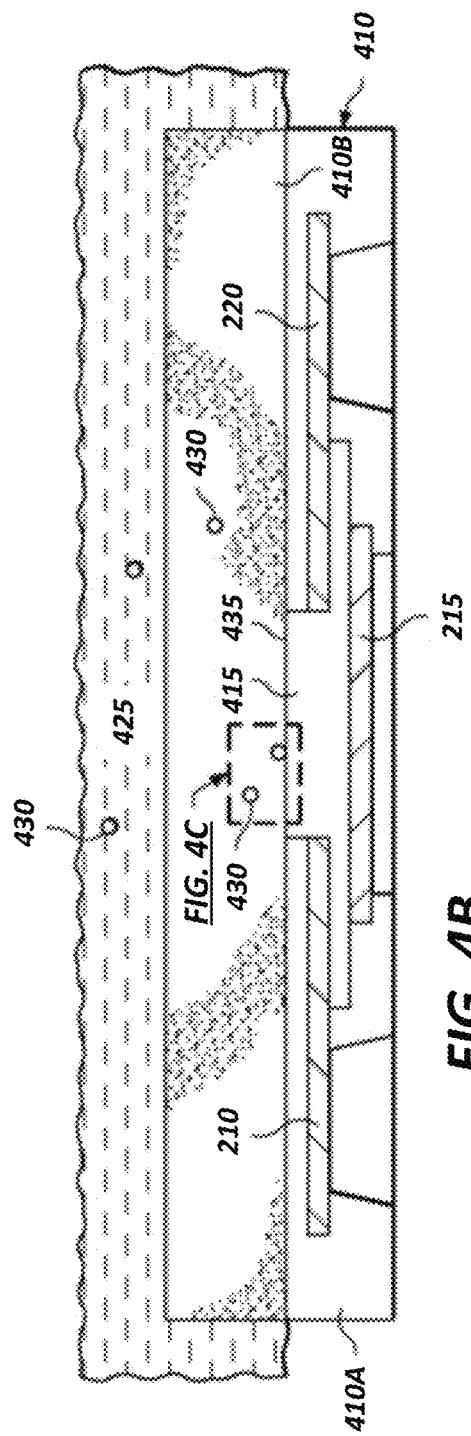
Figure 4C:
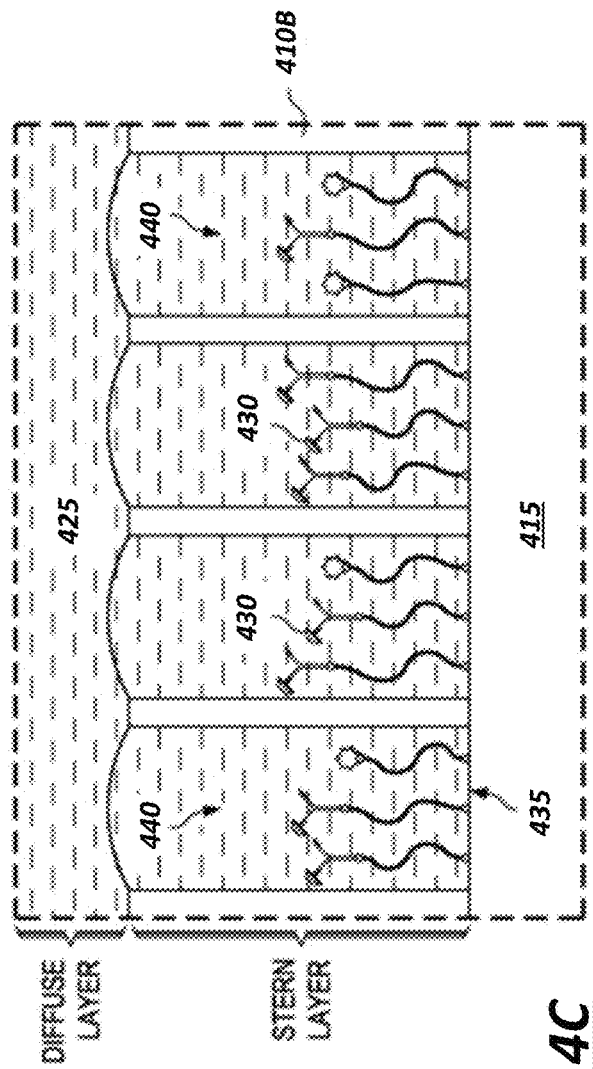

FIGS. 4A-4C are simplified block diagrams illustrating a biosensing system 205 for facilitating biosensing using electron-ionic mechanisms at fluid-sensor interfaces in accordance with one example embodiment; FIG. 4B is a cross-section along axis B-B'; and FIG. 4C is an example detail of the cross-section. FIG. 4A illustrates a biosensing system 205 comprising a biosensor 405 including a substrate 410, a sensing element 415, a plurality of electrodes 210, 215, 220, and an output 420 comprised of two components, baseline 420A and response 420B.

A transverse voltage may be applied across some of electrodes (e.g., 210 and 220); an orthogonal voltage may be applied across other electrodes (e.g., 210 and 215). Electrodes (e.g., 210 and 220) across which the transverse voltage is applied may be referred to as "transverse electrode"; electrodes (e.g., 210 and 215) across which the orthogonal voltage is applied may be referred to as "orthogonal electrodes". In a general sense, "transverse" and "orthogonal" refer to direction of electric fields produced by the respective voltages; in various embodiments, the electric field produced by the transverse voltage is perpendicular to the electric field produced by the orthogonal voltage. In some embodiments, the transverse voltage may comprise direct current (DC) voltage and the orthogonal voltage may comprise alternating current (AC) voltage. In other embodiments, the transverse voltage may comprise AC voltage, and the orthogonal voltage may comprise DC voltage. In yet other embodiments, the transverse voltage may initially comprise AC voltage, which may be switched to DC voltage, and the orthogonal voltage may comprise AC voltage.

Baseline 420A comprises impedance, or capacitance, or current measured across orthogonal electrodes 210 and 215 and establishes a baseline value for the respective measurement; response 420B comprises impedance, or capacitance, or current measured across transverse electrodes 210 and 220. In various embodiments, comparison between baseline 420A and response 420B can indicate a signal-to-noise ratio (SNR) of the measurements and provide detection and/or measurement of concentration of an analyte 430 in a fluid 425.

Substrate 410 generally allows for fluid containment such that a portion of fluid 425 comprising analyte 430 is in contact with sensing element 415 at a fluid-sensor interface 435, as indicated in FIG. 4B. Note that fluid containment is in three dimensions, for example, both vertically and laterally (e.g., perpendicular and parallel to sensing element surface.) Fluid-sensor interface 435 comprises a zone of interaction between sensing element 415 and fluid 425. In some embodiments, fluid-sensor interface 435 comprises a surface of sensing element 415 in contact with fluid 425; in other embodiments, fluid-sensor interface 435 comprises an additional layer of linker molecules that are bound to the surface of sensing element 415; in yet other embodiments, fluid-sensor interface 435 comprises an additional layer of capture probes that bind to the linker molecules. In yet other embodiments, fluid-sensor interface 435 additionally comprises a layer of fluid 425 including an electrical double layer (EDL).

In some embodiments, as indicated in FIG. 4B, substrate 410 may comprise two separate portions, indicated as 410A and 410B. In an example embodiment, portion 410A comprises a hydrophobic biocompatible material (e.g., Parylene™) and portion 410B comprises a porous biocompatible hydrophilic membrane (e.g., polyimide, polyamide, nylon, alumina, polycarbonate, polymer, ceramic, etc.). In various embodiments, portion 410A may prevent direct interaction between fluid 425 and electrodes 210, 215, 220, for example, providing dielectric separation (e.g., electrical isolation) of electrodes 210, 215, 220 from fluid 425. In some embodiments, portion 410B may provide a fluid containment zone allowing analyte 430 of fluid 425 to bind to sensing element 415 at fluid-sensor interface 435.

Some of electrodes 210, 215, 220 (e.g., 210 and 220) may be located on one plane, and the other electrodes (e.g., 215) may be located on another, different plane. In an example embodiment, transverse electrodes 210 and 220 may be located on a first plane of sensing element 415 and orthogonal electrode 215 may be located on a second plane of sensing element 415 parallel to and removed from the first plane.

To explain the fluid containment in more detail, as indicated in FIG. 4C, portion 410B may comprise pores 440 that provide a fluid containment zone allowing analyte 430 to bind to sensing element 415 at fluid-sensor interface 435 in the presence of an electric field. In some embodiments, pores 440 may comprise nanopores (e.g., diameter or size in the order of nanometers). In various embodiments, the electric field produced by the orthogonal voltage causes reversible aggregation of analyte 430 in fluid 425 into planar aggregates adjacent to fluid-sensor interface 435. The planar aggregation disassembles when the electric field is removed. In confined geometries, as in pores 440, the surface charge distribution on sensing element 415 and topography of bounding electrodes 210 and 220 may determine a nature of electron-ion interaction at fluid-sensor interface 435. The planar aggregation can include organization similar to self-assembly producing partial coverage, monolayer coverage or stretched coverage.

In various embodiments, fluid 425 wicks through pores 440 to make contact with sensing element 415 at fluid-sensor interface 435. In a general sense, when sensing element 415 having surface charge is immersed in fluid 425 containing ions, a diffuse ion cloud, called the "stern layer" forms in fluid 425 to screen (e.g., neutralize) sensing element 415's surface charge. Beyond the stern layer is a diffuse layer comprising ions providing an electrical gradient within fluid 425. The arrangement of a layer of (immobile) charges in the stern layer and the screening cloud of (mobile) counter-ions in the diffuse layer of fluid 425 is referred to as the electrical double layer (EDL). As noted previously, fluid-sensor interface 435 comprises the EDL. In the EDL of small but finite thickness, fluid 425 is not electroneutral. Consequently, electric fields acting on the EDL will set in motion ions in the diffuse layer, and these will in turn entrain surrounding fluid 425. The resulting flow fields reflect the spatial distribution of ionic current in fluid 425.

The diffuse layer may be polarized by the orthogonal electric field (i.e., the electric field produced by the orthogonal voltage) to effect charge perturbation associated with detection of target species of analyte 430 in fluid 425. The effective ionic content of the combination of the stern layer and the diffuse layer acts as a screen (e.g., charge screening) preventing the target species of analyte 430 from travelling to and binding to sensing element 415. However, excluded volume effect (e.g., 'excluded volume' of a molecule is the volume that is inaccessible to other molecules in the system as a result of the presence of the molecule) and macromolecular crowding from non-specific target species in the confined spaces (e.g., pores 440) can minimize such charge screening. Embodiments of biosensing system 205 can facilitate multiple target species detection in varying fluids (e.g., by providing multiple different affinity capture probes corresponding to the different species within the same sensor device); analyte 430 may comprise target species with no charge, high charge or low charge and fluid 425 may have with varying polarity levels within the broad scope of the embodiments.

Turning to FIGS. 5A-5C, simplified block diagrams 500*a-c* are shown illustrating example details of a biosensor 405. Electrodes 210, 215, 220 may comprise various nanostructures in a planar dimension. Spatial patterning of electrodes 210, 215, 220 can affect the placement and shape of the planar aggregation of analyte 430 at fluid-sensor interface 435, thereby affecting the sensitivity of biosensor 405. For example, the specific shape of electrodes 210 and 215 can affect the impedance and thereby the ionic current in fluid 425 at the vicinity of fluid-sensor interface 435.

In FIG. 5A, electrodes 210 and 215, across which the transverse voltage is applied may be situated on the same plane. Each of electrodes 210 and 215 may comprise digits 505 that may extend over sensing element 415. Digits 505 may be parallel along the length and face each other over sensing element 415. Digits 505 may be tailored for particular electrical modulation properties desired for specific target species of analyte 430. For example, in FIG. 5B, each of electrodes 210 and 215 may comprise digits 505 that are offset from each other along their widths and overlap along their lengths. In FIG. 5C, each of electrodes 210 and 215 may comprise a plurality of interleaving digits 505, overlapping along their lengths and offset along their widths. Note than any number of digits 505 (or other design features of electrodes 210, 215, 220) may be included within the broad scope of the embodiments.

In biosensors implementing the three-electrode configuration, such as a configuration where one orthogonal electrode on the back of the semiconductor and two lateral electrodes on the top of the semiconductor as shown in examples discussed herein (as well as other example electrodes illustrated and discussed, for instance, in U.S. patent application Ser. No. 14/946,899 or PCT Patent Application PCT/US17/57478), a direct current (DC) field may be applied along the orthogonal electrode to achieve electrophoretic modulation of the transport and diffusion of charged species in adsorbed sweat within the RTIL wicked nanoporous substrate towards the functionalized sensing surface, thus electrically screening out/in of non-specific versus specific charged species. Such a gating effect would result in pinning the height of the EDL at the functionalized sensor electrode/RTIL electrolyte interface whose capacitance (Cdl) is the result of aggregation of the various charged species at the interface. This Cdl is the sum of the series capacitance due to the "compact layer" also known as the "stern layer" immediately formed near the functionalized semiconducting oxide sensor interface and the capacitance due to the "diffuse layer" formed in the bulk RTIL electrolyte. Therefore, applying an alternating current (AC)-based adaptive electrochemical impedance spectroscopy (AEIS) to the lateral electrodes will enable detection and quantification of the amount of target analytes in adsorbed sweat when presented to the functionalized sensor electrode with the target specific capture probes. The resulting binding is electrically characterized by measuring changes to the capacitive impedance (Zimag and thus Cdl) over a range of frequencies across the two lateral electrodes. This method of device operation may enable achieving sensitivity as well as specificity in detection of multiple analytes.

The use of RTIL in an example biosensor can increase the electrical double layer length and also allows for the dielectric tuning between over screening and overcrowding of charges accumulating at the sensor surface towards achieving long term stability (24 hrs to 2 weeks) especially that of protein based antibodies bound to the sensor surface during the functionalization assay protocol steps, highly specific affinity binding to the target analyte (e.g., 99% accuracy), and high sensitivity (e.g., 99% measure) in detection of very low concentrations of target analyte from very low (sub microliter) to very high (e.g., 1000 microliters) of sample volumes associated with various use conditions.

A bioanalytic system may utilize biosensors, such as those described above, to implement a materials-based approach to demonstrate the utility of wearable physiological sensors for obtaining diagnostic information about the wearer. For instance, materials engineering may be utilized to design and fabricate conductor/semiconductor layers on an insulating flexible nanoporous substrate, which may be enhanced through optimized RTIL chemistry and formulation for electrophoretic charge transport and diffusion across the nanoporous membrane. Further, such implementations may enable non-faradic simultaneous label-free detection using AEIS of the multiple, specific target trace species in body fluids. Surface engineering of the semiconducting oxides with target specific capture probes and their characteristic changes in capacitive impedance to applied electrical fields may be used to achieve enhanced selectivity and sensitivity in detection of each of the specific analytes in body fluids. The outputs from the EDL modulated biosensor device stack may be utilized to produce a combinatorial digital response representative of physiological conditions towards lifestyle monitoring. For instance, key mechanisms may be tuned that influence electrode/electrolyte interactions in sweat and examine the sensor analytical performance parameters; cross reactivity noise (CRN), zero dose threshold (ZDT), limit of blank (LoB), limit of detection (LoD), range of detection (RD), sensor hysteresis (SH) for varying conditions of pH and ionic content of sweat, among other example metrics.

In some implementations, to improve the stability and reliability of the bound capture probes to functionalized semiconducting oxide surface, RTILs may be introduced into the substrate of the biosensor device(s) to serve as an electrolyte solvent buffer containing the target specific capture probes antibodies and that will conjugate with the functionalized semiconducting oxide surface during the immunoassay steps and also provide stability of the bound target specific capture probe antibodies during subsequent storage and handling and from exposure to environment. In simple electrolyte solvent solutions, the protein charge is determined by the equilibrium protonation of hydroxyl- and amino-groups and depends sensitively on the pH of the environment, whose variations can even reverse the sign of the overall charge. In RTILs dispersion energy, ion size, and additional H-bonding sites also come into play in determining protein characteristics. Unlike molecular solvents that are charge neutral, RTILs are molten salts at room temperature composed solely of polyatomic cations and anions. The properties of RTILs can be changed according to the requirement by modifying their constituents (i.e., cation and anion). Although they stabilize the protein over a wide range of temperature, the thermal stability of proteins depends on the appropriate choice of RTILs, as proteins are not homogeneously stable in all type of RTILs. The stability and activity of proteins is affected by many factors such as polarity, hydrophilicity vs. hydrophobicity and hydrogen-bond capacity of RTILs, excipients, and impurities, among other example considerations.

Figure 6B:
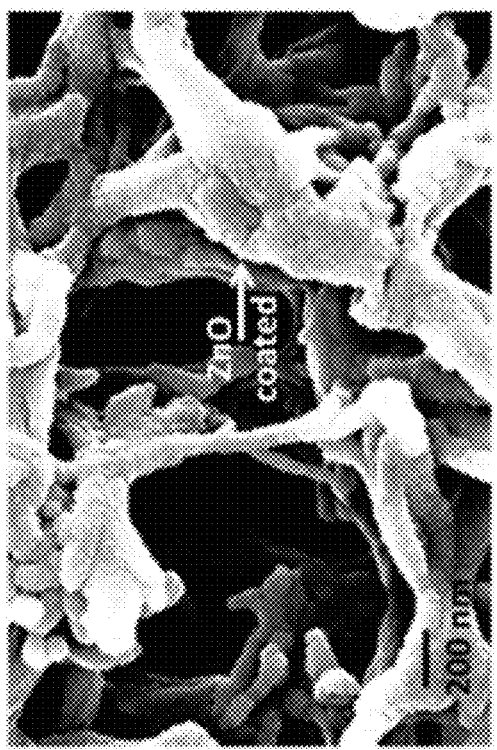
FIGS. 6A-6B show example micrograph images illustrating an example nanotexturized fabric that may serve as the base for an example sensor device.
Figure 6A:
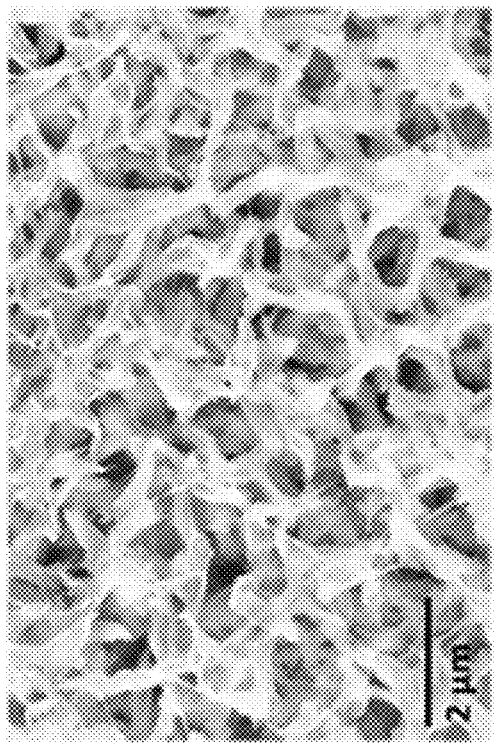
Figures 6C, 6D:
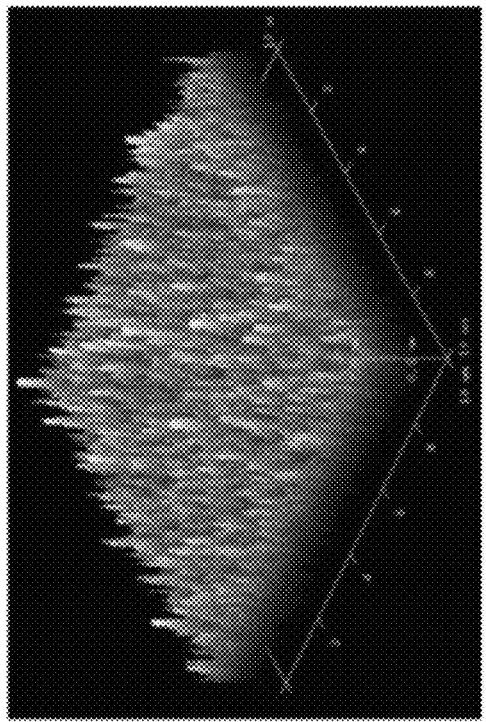
FIG. 6C is a table illustrating example parameters of an example nanotexturized substrate of a biosensor.
FIG. 6D is an image showing the physical roughness of an example engineered nanotextured textile substrate enabling nanoscale fluid confinement suitable for biosensing.
Figures 7A, 7B:
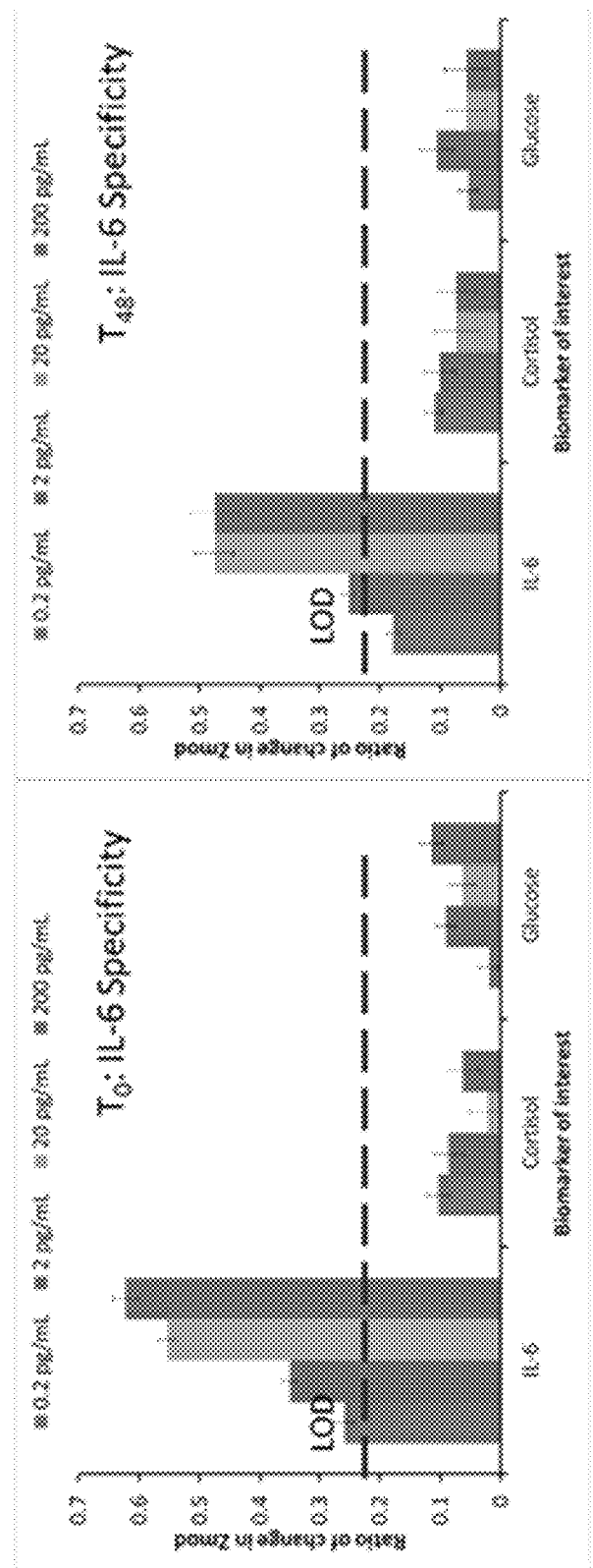
FIGS. 7A-7D are graphs illustrating performance of an example RTIL-infused biosensor.
Figures 7C, 7D:
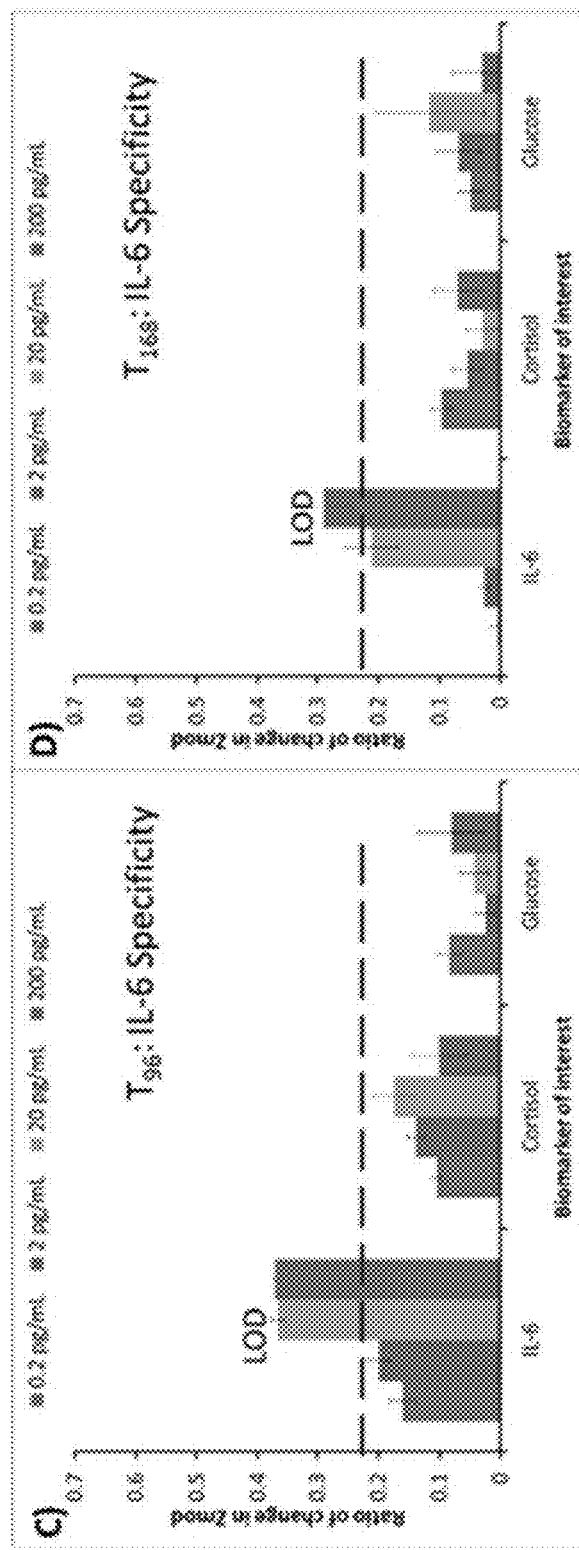

FIGS. 6A-6B example micrograph images illustrating an example nanotexturized fabric that may serve as the base for an example sensor device. For instance, FIG. 6A is the scanning electron micrograph 600a of an example porous polymer textile fabric which is engineered to enable confinement of the fluid. FIG. 6B is a micrograph 600b shows the conformal coating of the semiconducting material onto the porous fabric to generate the formation of the active sensing area. Upon functionalization of the semiconducting surface with the desired affinity capture probes, efficient binding of low concentrations of target species present within the confined fluids to the target specific affinity capture probes is enabled thus providing enhanced sensitivity of the corresponding biosensor. FIGS. 6C-6D shows the physical parameter range of an example nanotextured textile fabric that enables fluid confinement in the nanoscale (such as shown in FIG. 6A) leading to enhanced sensitivity of trace concentrations of target analyte species. For instance, FIG. 6C is a table 600c illustrating example parameters of such a nanotexturized substrate. FIG. 6D is an image 600d showing the physical roughness of the engineered nanotextured textile substrate towards enabling nanoscale fluid confinement suitable for biosensing.

FIGS. 7A-9B are graphs illustrating the effect of integrating an RTIL into biosensor implementations, such as those shown and described herein. These graphs represent example data showing the benefits of applying RTIL (e.g., two types: BMIM[BF4] and Choline[DHP]) within a biosensor device to realize improved sensitivity, temporal stability, and specificity of biosensor for the detection of an inflammatory biomarker Interleukin-6 (IL-6) and stress biomarker cortisol. For instance, these example results demonstrate in particular that, while both types of RTIL enhance the biosensor performance over no RTIL, BMIM[BF4] RTIL is a better choice for Cortisol biosensor and Choline [DHP] is a better choice for Interleukin-6 biosensor, among other example implementations. Furthermore, this example data also establishes the stability in detection of the inflammatory biomarker Interleukin-6 (IL-6) over 48 hours and up to 96 hours since the start of functionalization of the semiconducting sensing material surface. This is relevant for continuous and real-time sensing for wearable diagnostic sensors.

In light of the above protein-based studies, the use of RTIL interactions in these application can be summarized as follows: (i) because of charge and dispersion forces, cations tend to be more closely coordinated to proteins than anions; (ii) the relative role of the anions and cations, however, depends on the protein charge, that in turn changes with (at least) the pH of the solution/environment; (iii) the ion most closely coordinated to the protein body interacts by a combination of Coulomb and short-range forces (dispersion H-bonding, steric interactions) and thus is responsible for specific effects arising from the protein-RTIL interactions.

In this disclosure, an improved biosensor is described that can function in any volume of human body fluid (with emphasis on perspired ambient human sweat in contrast to other state-of-art that relies on stimulated sweat) without under or over saturation. Sensor response to ≥10-18 atto-molar sensitivity may be realized due to an increase in the length of the Electrical Double Layer (EDL) formed on the sensor surface by a factor of 10× to 1000×, which increases the physical affinity binding sensing region from angstroms to 100s of nanometers that can be measured and correlated to develop calibrated quantitative analysis using impedance spectroscopy. Further, the lifetime of such sensors (e.g., as integrated in a wearable sensor device) may be from 24 hours to up to 2 weeks due to the use of RTILs that enhances and ensures the stability of the bound protein antibodies needed for the detection of the target biomarkers. This may effectively resolve one of the biggest challenges in affinity-based biosensing using bound proteins, aptamers, etc. as these biological agents tend to denature rapidly at ambient use conditions. The use of RTILs as proposed in this invention helps extend the shelf life of the test (e.g., well beyond 168 hours), which may be very desirable in for wearable affinity based biosensors. The use of RTILs may also further enhance the EDL contributing to both enhanced specificity and sensitivity. Selectivity and sensitivity of the sensor can be tuned, for instance, to 99% accuracy irrespective of the complexity of the body fluid. Accordingly, multiple different analytes can be detected (e.g., up to 8) from body fluid volumes as low as 1 microliter using the same sensor device, among other example implementations utilizing principles and embodiment similar to those described herein.

According to various embodiments, the devices described herein are adapted such that analysis of a species of interest may be conducted, in one embodiment, in the devices described herein, or in another embodiment, downstream of the devices described herein, for example, in a separate server coupled to the device. It is to be understood that the devices described herein may be useful in various analytical systems, including bioanalysis microsystems. Although the biosensor system has been described with respect to particular devices and methods, it will be understood that various changes and modifications can be made without departing from the scope of the embodiments.

Note that in this document, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Furthermore, the words "optimize," "optimization," and related terms are terms of art that refer to improvements in speed and/or efficiency of a specified outcome and do not purport to indicate that a process for achieving the specified outcome has achieved, or is capable of achieving, an "optimal" or perfectly speedy/perfectly efficient state.

In general, computing systems, which interface with a biosensor via a wired or wireless communication channel can include electronic computing devices operable to receive, transmit, process, store, or manage data and information associated with the biosensor and other subsystems of the computing system. As used in this document, each of the terms "computer," "processor," "processor device," "microcontroller," or "processing device" is intended to encompass any suitable data processing apparatus. For example, while the microcontroller may be implemented, in some examples, as a single device within the computing system, in other implementations the processing functionality of the system may be implemented using a plurality of computing devices and processors, such as a fog computing system, server pools, a cloud computing system, or other distributed computing system including multiple computers. Further, any, all, or some of the computing devices may be adapted to execute any operating system, including Linux, UNIX, Microsoft Windows, Apple OS, Apple iOS, Google Android, Windows Server, etc., as well as virtual machines adapted to virtualize execution of a particular operating system, including customized and proprietary operating systems.

In some implementations, all or a portion of a computing platform may function as a wearable device, standalone biosensor device, or other sensor device. A sensor device may connect to and communicate with other computing devices through wired or wireless network connections. For instance, wireless network connections may utilize wireless local area networks (WLAN), such as those standardized under IEEE 802.11 family of standards, home-area networks such as those standardized under the Zigbee Alliance, personal-area networks such as those standardized by the Bluetooth Special Interest Group, cellular data networks, such as those standardized by the Third-Generation Partnership Project (3GPP), and other types of networks, having wireless, or wired, connectivity. For example, an endpoint device may also achieve connectivity to a secure domain through a bus interface, such as a universal serial bus (USB)-type connection, a High-Definition Multimedia Interface (HDMI), or the like.

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Although the present disclosure has been described in detail with reference to particular arrangements and configurations, these example configurations and arrangements may be changed significantly without departing from the scope of the present disclosure. For example, although the present disclosure has been described with reference to particular chemical interactions involving ZnO, the system may be applicable to other interactions and semiconducting materials. Moreover, although the system has been illustrated with reference to particular secondary elements and operations that facilitate the biosensing process, these secondary elements, and operations may be replaced by any suitable architecture or process that achieves the intended functionality described herein.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

The invention claimed is:

1. An apparatus comprising:
a porous substrate having a first surface and an opposing second surface, the second surface to contact a subject to absorb fluid carrying an analyte from the subject;
a layer of semiconducting oxide coated on a portion of the first surface, the semiconducting oxide functionalized to conjugate with the analyte;
two or more electrodes attached to the first surface of the porous substrate and in direct contact with the layer of semiconducting oxide; and
a Room-Temperature Ionic Liquid (RTIL) between the first surface and the second surface, wherein:
the layer of semiconducting oxide is in direct contact with the RTIL and the electrodes,
the RTIL does not contain elements that bind with the analyte, and
the RTIL is to contain the fluid carrying the analyte between the first surface and the second surface for measurement by the electrodes.

2. The apparatus of claim 1, wherein the semiconducting oxide comprises an array functionalized to conjugate with a plurality of different analytes including the analyte.

3. The apparatus of claim 1, wherein the two or more electrodes comprises at least three electrodes.

4. The apparatus of claim 1, wherein the semiconducting oxide comprises thin films functionalized with particular linkers and affinity capture probes to bind to the analyte.

5. The apparatus of claim 4, wherein the affinity capture probes functionalized on the semiconducting oxide is surrounded by the RTIL.

6. The apparatus of claim 1, wherein the semiconducting oxide comprise one of Zinc Oxide (ZnO) or Graphene Oxide.

7. The apparatus of claim 1, wherein the porous substrate comprises a flexible substrate sheet to contact skin of a user.

8. The apparatus of claim 1, wherein the fluid comprises bodily fluid.

9. The apparatus of claim 1, further comprising a wearable biosensor, and the wearable biosensor comprises the porous substrate and electrodes to implement a sensor on the wearable biosensor.

10. A method comprising:
absorbing a fluid into a porous substrate of a biosensor device, wherein:
the porous substrate has a first surface and an opposing second surface,
the second surface is to contact the fluid,
a portion of the first surface is coated with semiconductor elements functionalized to conjugate with an analyte in the fluid,
the biosensor device further comprises two or more electrodes attached to the first surface of the porous substrate,
the semiconductor elements are between the two or more electrodes and the second surface,
a Room-Temperature Ionic Liquid (RTIL) is pre-deposited within the porous substrate between the semiconductor elements and the second surface,
the RTIL does not contain elements that bind with the analyte, and
the RTIL is in contact with the semiconductor elements; and sensing the analyte using the biosensor device.

11. The method of claim 10, wherein sensing the presence of the analyte using the biosensor device further comprises:
applying a voltage to the two or more electrodes; and
measuring at least one of impedance or capacitance across the electrodes to determine presence of the analyte in the fluid.

12. The method of claim 10, wherein the semiconductor elements comprises thin films functionalized with particular linkers and affinity capture probes to bind to the analyte.

13. The method of claim 12, wherein the affinity capture probes functionalized on the semiconductor elements is surrounded by the RTIL.

14. The method of claim 10, wherein the porous substrate comprises a flexible substrate sheet to contact skin of a subject.

15. The method of claim 10, wherein the presence of the analyte is captured during passive monitoring of a subject.

16. The method of claim 10, wherein the presence of the analyte is captured during active monitoring of a subject.

17. A system comprising:
a microcontroller; and
a biosensor device coupled to the microcontroller, wherein:
the biosensor device comprises a porous substrate and two or more electrodes,
the porous substrate has a first surface and an opposing second surface,
semiconductor elements functionalized to conjugate with an analyte are coated on a portion of the first surface,
the second surface of the porous substrate is to absorb fluid from a subject,
the fluid is capable of carrying the analyte,
a Room-Temperature Ionic Liquid (RTIL) is pre-absorbed into the porous substrate between the first surface and the second surface,
the RTIL is in contact with the semiconductor elements,
the RTIL does not contain elements that bind with the analyte,
the two or more electrodes are on the first surface of the porous substrate, and
the semiconductor elements are between the two or more electrodes and the RTIL.

18. The system of claim 17, wherein the semiconductor elements comprises thin films functionalized with particular linkers and affinity capture probes to bind to the analyte.

19. The system of claim 18, wherein the affinity capture probes functionalized on the semiconductor elements is surrounded by the RTIL.

\* \* \* \* \*